(12) United States Patent
Fischell et al.

(10) Patent No.: US 12,397,135 B1
(45) Date of Patent: Aug. 26, 2025

(54) RAPID EXCHANGE (MONORAIL) GUIDE WIRE SYSTEM FOR RAPID DELIVERY OF GUIDE WIRE TO A BLOOD VESSEL

(71) Applicants: Tim A. Fischell, Kalamazoo, MI (US); David R. Fischell, Fair Haven, NJ (US)

(72) Inventors: Tim A. Fischell, Kalamazoo, MI (US); David R. Fischell, Fair Haven, NJ (US)

( * ) Notice: Subject to any disclaimer, the term of this patent is extended or adjusted under 35 U.S.C. 154(b) by 0 days.

(21) Appl. No.: 18/451,392

(22) Filed: Aug. 17, 2023

(51) Int. Cl.
*A61M 25/09* (2006.01)
*A61M 25/01* (2006.01)

(52) U.S. Cl.
CPC ..... *A61M 25/09* (2013.01); *A61M 2025/0177* (2013.01); *A61M 2025/0183* (2013.01); *A61M 2025/09008* (2013.01)

(58) Field of Classification Search
CPC .......... A61M 25/09; A61M 2025/0177; A61M 2025/0183; A61M 2025/09008
See application file for complete search history.

(56) References Cited

U.S. PATENT DOCUMENTS

| | | | | |
|---|---|---|---|---|
| 5,117,838 A | * | 6/1992 | Palmer | A61M 25/0905 600/585 |
| 6,139,540 A | * | 10/2000 | Rost | A61M 25/09 600/585 |
| 2012/0150271 A1 | * | 6/2012 | Fischell | A61M 25/09 604/528 |
| 2012/0210569 A1 | * | 8/2012 | Schmitt | A61M 25/09041 29/700 |
| 2020/0129317 A1 | * | 4/2020 | Gupta | A61M 25/09 |

* cited by examiner

*Primary Examiner* — Michael R Bloch
*Assistant Examiner* — Nidhi N Patel
(74) *Attorney, Agent, or Firm* — Shay Glenn LLP

(57) ABSTRACT

A rapid exchange guide wire system for rapid delivery of a guide wire to a blood vessel. The system has a main guide wire and rapid a rapid exchange tube attached to the main guide wire near a distal end of the main guide wire. The rapid exchange tube has a lumen which extends in a longitudinal direction and is configured to permit the rapid exchange tube to be reversibly displaceable in the longitudinal direction over a medical device having a cylindrical portion The medical device may be a guide wire, balloon angioplasty catheter, stent delivery catheter, atherectomy catheter, intravascular ultrasound catheter, blood flow measurement wire, optical coherence tomography catheter, or a stent-on-wire catheter.

19 Claims, 9 Drawing Sheets

RAPID EXCHANGE (MONORAIL) GUIDE WIRE SYSTEM FOR RAPID DELIVERY OF GUIDE WIRE TO A BLOOD VESSEL

BACKGROUND OF THE INVENTION

Percutaneous intervention (PCI) in peripheral and coronary arteries is a commonly performed procedure. In many cases there is a need to quickly deliver a new, or a second guide wire (sometimes called a buddy wire) to a distal location in a blood vessel such as a coronary artery. In many cases this requires placing an over-the-wire-catheter with a continuous guide wire lumen over an existing guide wire, and then replacing the initial wire by removing it and re-inserting the new wire through the catheter. Different types of catheters for this include over-the-wire balloon angioplasty catheters and microcatheters.

A primary reason for a buddy wire is to replace a wire with one set of characteristics with one with a different set of characteristics that are needed to conduct the next step in the PCI procedure. For example, a highly deliverable workhorse wire might be used to access a distal site in a coronary artery but a very stiff wire could be needed for the next step in penetrating a chronic total occlusion (CT)) or advancing an atherectomy or angioplasty catheter. Additionally, after use of a stiff wire, if a workhorse type wire is needed to access additional portions of the anatomy, then one can replace a stiff wire with a buddy workhorse wire.

In the case of coronary atherectomy with a device such as the Rotablator or orbital atherectomy catheter, it is often difficult to perform primary wire delivery of the Rota-wire or Viper wire specialized wire. In these cases, once again, one most often has to place a better (workhorse) wire to the distal coronary artery, then add the step of delivering an over-the-wire catheter over that first wire, and then proceed to removing the workhorse wire replacing it with the Rota-wire, and then doing another half exchange to remove the catheter prior to atherectomy. This is time-consuming, costly, with added risks, and is cumbersome. In this scenario, after the atherectomy one has to reverse this process to remove the atherectomy wire and replace it with a standard "workhorse" wire.

In another scenario one can have a need for placing a second guide wire down a coronary to help straighten curves in that vessel to enhance the delivery of stiffer devices such as a coronary stent delivery catheter. This technique referred to as "buddy-wire" is used, but requires placing (steering) a second and often a stiffer wire along the same path as the first guide wire. This again is time consuming, expensive, and potentially risky.

In a third scenario one might use a recently developed stent on a wire system. This system has a "fixed guide wire". If one were to have a dissection at or near the area of balloon inflation and stent deployment one may want to rapidly place a guide wire in the distal coronary. Currently there is no system to allow the rapid delivery of a coronary guide wire over the shaft of an already placed balloon catheter or stent on a wire delivery catheter.

In a fourth scenario, a buddy wire system can be used for guiding catheter exchanges. It is not uncommon to have a small (0.014") coronary guidewire placed distally in a diseased vessel, and then to have difficulty delivering a balloon angioplasty catheter or stent to a more distal target site, related to a poor guiding catheter shape with inadequate "backup." Historically, one often tries to fight through this, and resist the urge to place a new guiding catheter with a better shape because of the challenges and risks of removing your coronary guidewire and exchanging to a new guiding catheter. In this final iteration of the buddy wire concepts we describe a buddy wire with 2 or more sections of different diameters. For example, the distal portion could be a flexible wire of 0.014" diameter transitioning to a larger (0.018") wire more in a central portion, and then transitioning to as large as a 0.035" stiff wire in the proximal portion. In one embodiment this multi-diameter wire may would have an inflatable balloon capability in the distal portion allowing balloon anchoring once the buddy wire is delivered distally in a coronary artery over the existing coronary guidewire. The inflation that would be performed on this exchange length (long) wire/catheter system can be done with a "removable" inflation device, such that the balloon can be inflated while a first guiding catheter is removed, then detached to allow one to slide the first guiding catheter off the proximal end of the wire; then reinflated after advancing a new (second) guiding catheter fully onto the exchange length system, to allow easy advancement of the new guiding catheter to the coronary over the exchange system. Once the new guiding catheter is in place, one can deflate the balloon and remove the monorail guide catheter exchange wire from the body.

SUMMARY OF THE INVENTION

The current invention envisions a Buddy Guide Wire (BGW) that can be delivered using a rapid exchange concept to deliver the BGW over a previously placed (primary) coronary guide wire to allow the rapid delivery through the correct path and lumen to a distal coronary or other blood vessel site. For example, one could rapidly deliver a workhorse BGW to a distal coronary artery in the any of the above scenarios. Although it is well known in the art to deliver a device (including rapid exchange device) over a guide wire, there has never been a system/device to allow the rapid delivery of a guide wire over another guidewire or a guide wire over a "device/catheter".

The current invention BGW is a "monorail" guide wire that can be delivered using a rapid exchange concepts, over a previously placed guide wire or catheter to facilitate PCI in a coronary artery or other blood vessel. For example, the following steps might be used:
1. Deliver a standard workhorse guide wire to a distal coronary in a case where one is planning Rotablator atherectomy,
2. Deliver in a rapid exchange fashion, a version of the present invention BGW configured as the stiff 0.009" guide wire used with Rotablator, "Rota-wire" that is now able to be delivered in a rapid exchange fashion over the shaft/body of the previously placed workhorse wire.
3. Retract the workhorse wire from the PCI site
4. Deliver the Rotoblator over the atherectomy BGW and
5. Perform rotational atherectomy.
6. Remove the atherectomy device
7. After performing the atherectomy one could then deliver a workhorse version of the BGW for use with balloon or stent delivery catheters, over the Rota-wire, and followed by removal of the atherectomy BGW to complete the PCI procedure.

This same concept could be used to very rapidly deliver a BWG with any desirable characteristics to a distal location over an existing previously placed first wire or catheter.

The same system concept could be used with a snap-on feature to allow one to very quickly and efficiently deliver a BGW or an embodiment called an Over Catheter BGW (OCBGW) over the shaft of a previously placed balloon angioplasty catheter or a stent delivery catheter shaft. In particular, this could be useful in the event of a dissection when using a stent on a wire/integrated stent delivery system that has only a fixed coronary guide wire on the end of the delivery system. In this case if there were a dissection one could "snap on" this monorail guide wire onto the shaft of a stent delivery catheter. This would allow one to rather rapidly place the BGW as a conventional workhorse version of a coronary guide wire distal to the dissection, with removal of the integrated stent delivery catheter, to allow further treatment of the blood vessel with conventional angioplasty or stenting.

Finally, a similar type of system could be used to rapidly deliver other guide wires to peripheral blood vessels, cerebral blood vessels, venous blood vessels, or other areas in the heart and blood vessels to enhance the speed and efficiency of guide wire delivery. One could deliver a coronary 0.014" wire over a peripheral 0.035" wire to use a coronary device for a peripheral lesion, or to deliver n 0.035" BGW over an 0.0014" coronary guidewire used to "wire" a very tight stenosis. These and other uses of such a BGW are anticipated.

One similarity of all the embodiments of the present invention BGW is that they have a rapid exchange tube (RXT) located at or near the distal end of the BGW. There are two types of RXTs; those that are a closed cylinder or those that have a slot to allow the RXT to snap over another device such as a standard guide wire or a catheter shaft. The inside diameter of the RXT would for any particular embodiment of the BGW would be sized for the device it is designed to track over. For example, a BGW embodiment designed to track over a standard coronary 0.014" diameter guide wire would have an RXT with an inside diameter of ~0.018". An RXT designed to go over a balloon angioplasty catheter would have an inside diameter of approximately 2 and 10 mils greater than the outside diameter of the catheter. For example, if the angioplasty catheter has an outside diameter of 0.032 inches, the inside diameter of the RXT might typically be 0.036 inches. To reduce product codes it is envisioned that one might have one version for over guide wire BGWs and one or two for over catheter BGWs. For example, one might have BGWs with RXTs having appropriate inside diameters to accommodate 0.014" or 0.035" guide wires, balloon angioplasty catheters and stent delivery catheters, respectively.

The terms rapid exchange and monorail will be used interchangeably herein to refer to a device that can be advanced over a guide wire or catheter where the device includes a lumen that is located near the distal end of the device but has a longitudinal length that is less than half of the length of the device.

The term snap-on will refer to the lumen of a rapid exchange or monorail device where the lumen used to be advanced over the guide wire or catheter can be placed concentrically over the guide wire or catheter without the need to slide it down from the proximal end over the guide wire or catheter. Such a snap-on approach may use either a lumen that is like a tube with a slot in it that does not go all 360 degrees around or that goes 360 degrees or more around but has a cut that allows it to be opened up and placed over the guide wire or catheter These and other advantages of this new invention will become apparent to people with ordinary skill in the art.

DETAILED DESCRIPTION OF THE DRAWINGS

Figure 1:
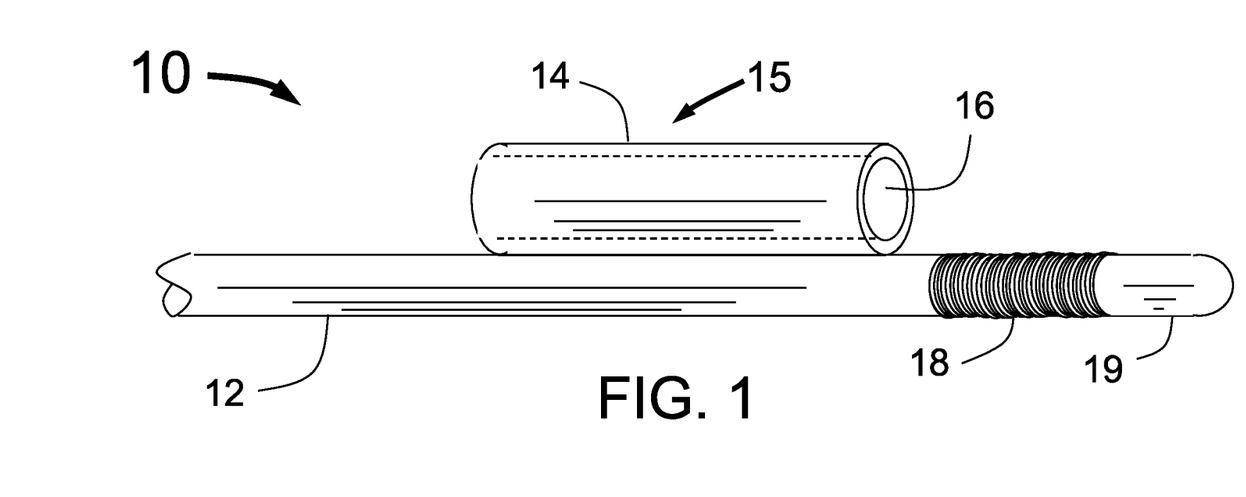
FIG. 1 is a schematic view of the present invention BGW.
Figures 7, 8, 9:
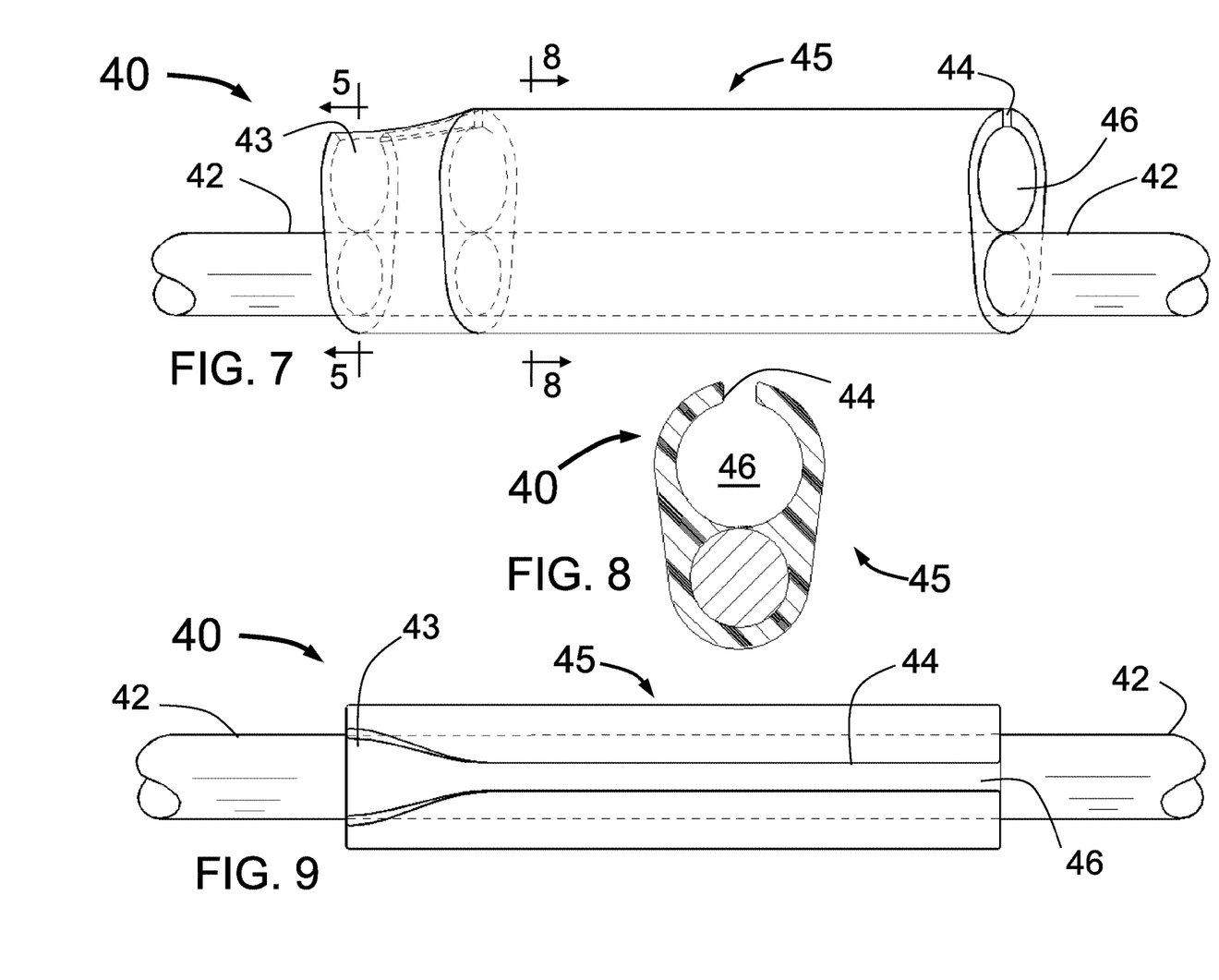
FIG. 7 is a schematic view of an alternate embodiment of the BGW a tapered slot in the RXT.
FIG. 8 is a cross sectional view of the BGW of FIG. 7 at section 8-8.
FIG. 9 is a top view of the BGW of FIG. 7.

FIG. 1 is a schematic view of the present invention Buddy Guide Wire (BGW) 10 having a Rapid Exchange Tube (RXT) 15 with outer tubular surface 14 and lumen 16. The BGW 10 has a main wire 12 with distal flexible section 18 and distal tip 19. The distal flexible section 18 can allow the distal portion of the BGW 10 to be pre-formed for better tracking through the coronary vasculature. In this embodiment the RXT 15 is attached to the BGW 10. The attachment method will depend on the materials used. For example, if the RXT 15 and main guide wire 12 are both metal, then welding, soldering or brazing would be a viable method for attachment. If the RXT 15 and main guide wire 12 are of different types of materials, adhesive bonding could be used. It is also envisioned that as shown in FIG. 7, a plastic RXT could be used that would have two lumens, a rapid exchange lumen and a lumen through which the main guide wire would be placed and bonded.

Figure 2:
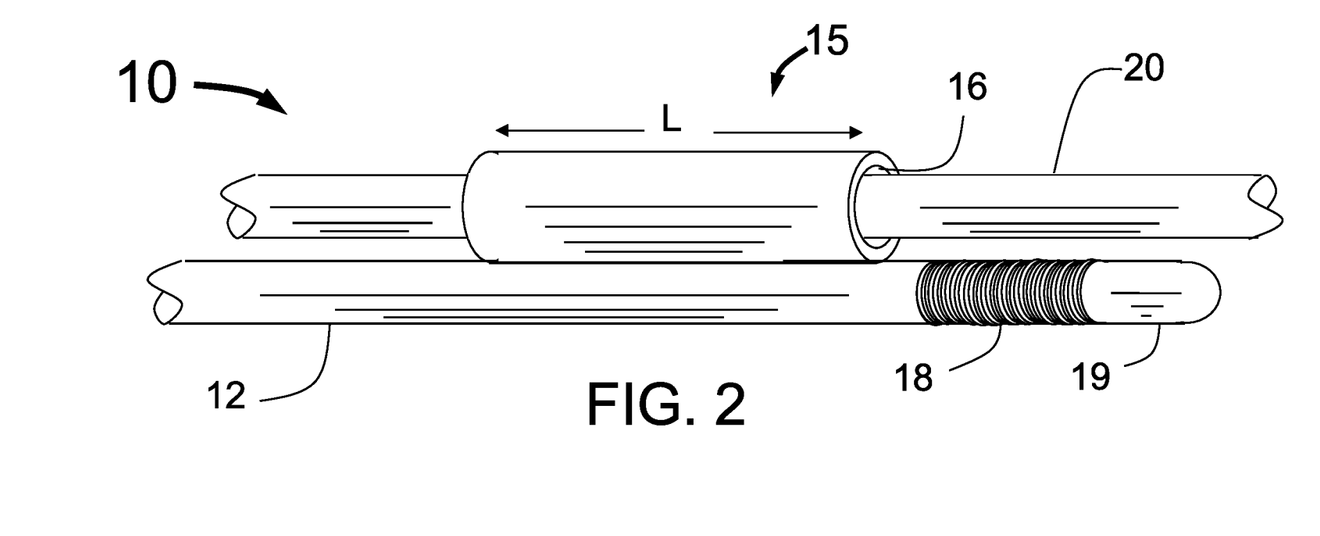
FIG. 2 is a schematic view of the present invention BGW being slid longitudinally over a previously placed guide wire.

FIG. 2 is a schematic view of the present invention BGW 10 being slid longitudinally over a previously placed guide wire 20 that runs coaxially through the lumen 16 of the RXT 15. This embodiment of the BGW 10 requires that the BGW 10 be slid over the previously placed guide wire from the proximal end of the previously placed guide wire.

The RXT 15 has a length L that will be between 5 mm and 10 cm with the ideal length of 1-2 cm. It is also envisioned that there could be 2 or more short RXTs spaced over a length of 1 to 5 cm so as not to stiffen the distal portion of the BGW.

Figure 3:
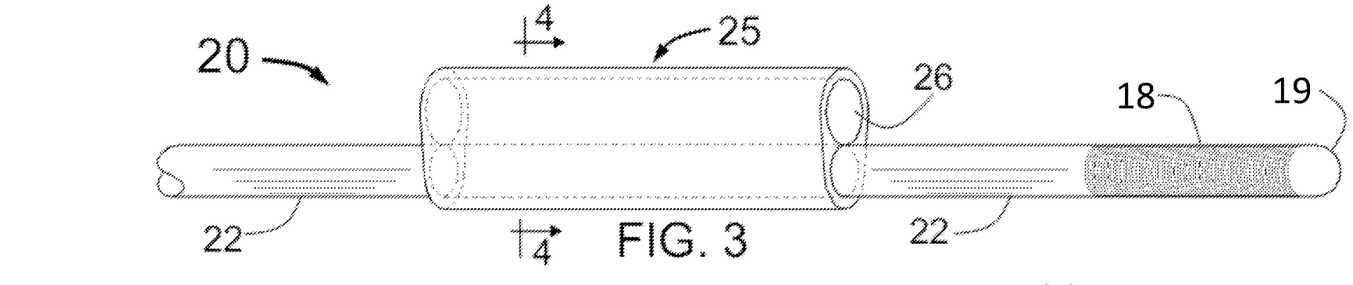
FIG. 3 is a schematic view of another embodiment of the BGW.

FIG. 3 is a schematic view of another embodiment of the BGW 20 having a rapid exchange tube (RXT) 14 that is slid coaxially over the main guide wire 22 and fixedly attached by use of an adhesive, welding, brazing or soldering depending on the materials used for the RXT 25 and main guide wire 22. It is also envisioned that the RXT 25 if made of a plastic material could be molded over the RXT 25. The RXT 25 has a guide wire lumen 26 through which a primary guide wire (not shown) can be placed.

Figures 4, 6:
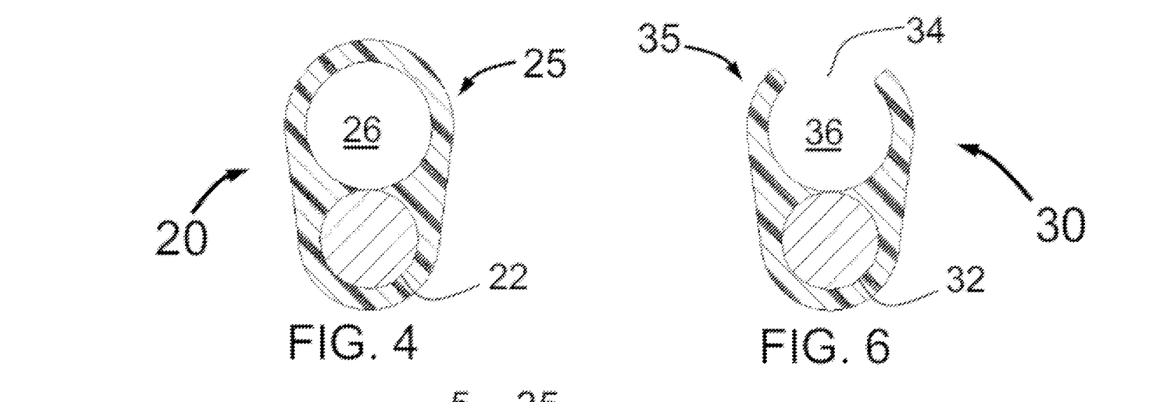
FIG. 4 is a cross sectional view of the BGW of FIG. 2 at section 4-4.
FIG. 6. is a cross sectional view of the alternate embodiment of the BGW of FIG. 5 at section 5-5 having a snap-on slot.

FIG. 4 is a cross sectional view of the BGW 20 of FIG. 2 at section 4-4 of the RXT 25. The RXT 25 has the guide wire lumen 26 and is shown attached to the main guide wire 22.

Figure 5:
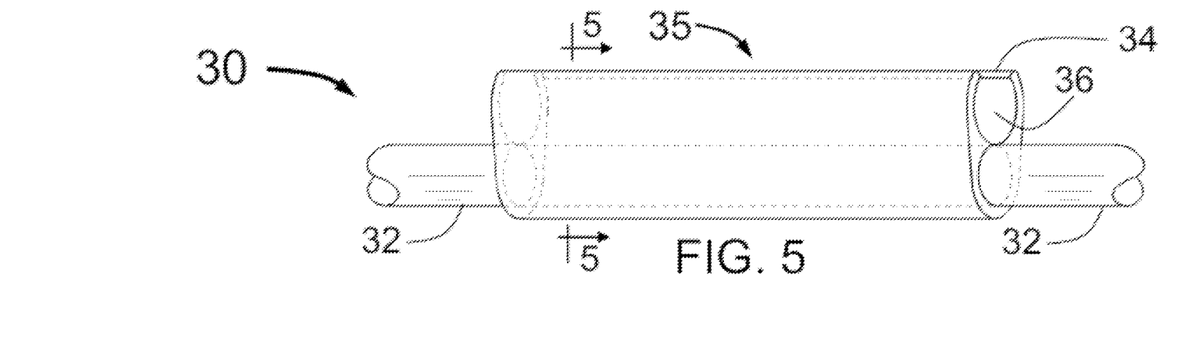
FIG. 5 is a schematic view of an alternative embodiment of the BGW having a snap-on slot.

FIG. 5 is a schematic view of an alternative embodiment of the BGW 30 having a main guide wire 32, an RXT 35 with a snap-on slot 34 and guide wire lumen 36. The advantage of the snap-on slot 36 is that the BGW 30 need not be slid over the proximal end of a primary guide wire (not shown) but can be pushed or snapped on to the primary wire by pushing the wire into the slot 34 until it pops or snaps into the guide wire lumen 36.

FIG. 6. is a cross sectional view of the alternate embodiment of the BGW 30 of FIG. 5 at section 5-5 having a snap-on slot 34 and guide wire lumen 36 in the RXT 35. The main guide wire 32 is shown attached coaxially within the RXT 35.

FIG. 7 is a schematic view of an alternate embodiment of the BGW 40 having a main wire 42, an RXT 45 with tapered snap-on slot 43 that narrows and connects to a uniform width slot 44. The purpose of the tapered slot 43 is facilitate making it easy to begin the sliding of a primary guide wire (not shown) into the slot 43 which will then because of the taper, allow the primary guide wire to push open the uniform width slot 44 as it is pushed in. Once the primary guide wire is pushed into the guide wire lumen 46, the narrow slot 44 resists the primary guide wire accidentally slipping out the guide wire lumen 46 as the BGW 40 is advanced through the vasculature. Such slipping out is more likely with a single wide slot such as shown for the RXT 35 of FIGS. 5 and 6.

It is envisioned that the tapered slot can be located at either the distal or proximal section of the RXT 45 or there could be a tapered section with a tapered slot 43 at both distal and proximal sections of the RXT 45.

FIG. 8 is a cross sectional view at 8-8 of the BGW 40 of FIG. 7 with guide wire lumen 46 and slot 44. It should be noted that the FIG. 5 shows a cross sectional view as seen at section 5-5 of FIG. 7.

FIG. 9 is a top view of the BGW 40 of FIG. 7 having main wire 42, an RXT 45 with guide wire lumen 46 and a tapered slot 42 that connects with a narrow slot 44.

Figure 10:
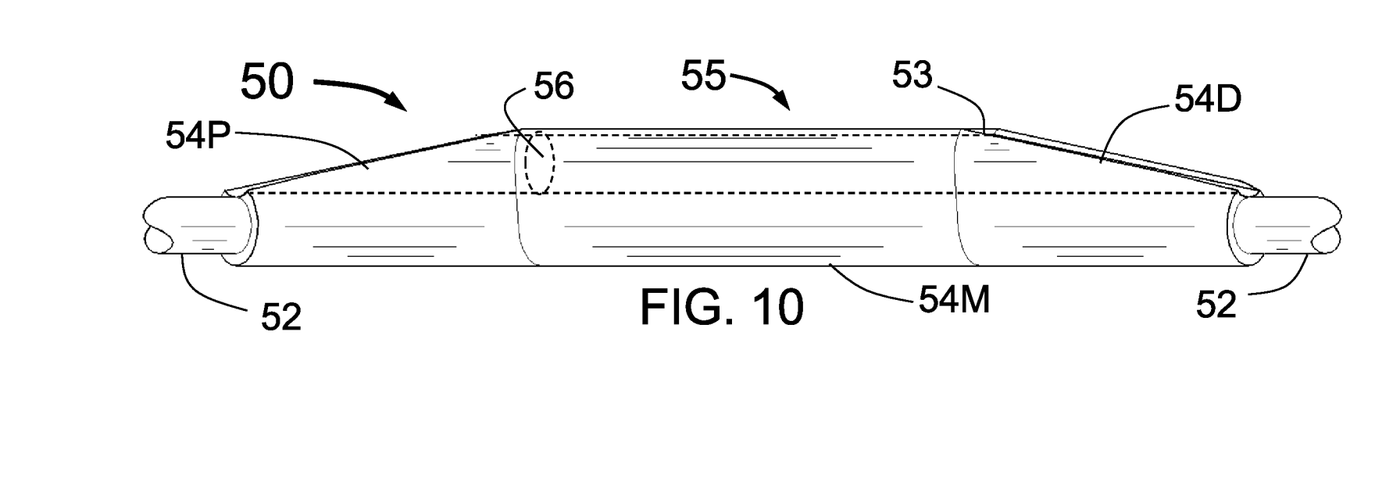
FIG. 10 is a schematic view of an additional BGW embodiment having a tapered RXT with a snap-on feature.

FIG. 10 is a schematic view of a BGW 50 with main guide wire 52, a tapered RXT 55 having a guide wire lumen 56, a tapered proximal section 54P, central section 54M and tapered distal section 54D. The tapered shape is designed to facilitate better tracking over a primary wire (not shown) as the tapered sections 54P and 54D will be less likely to catch or snag on an obstruction or sharp bend compared to the untapered RXTs 15, 25, 35, and 45 of FIGS. 1 through 9 allowing the entire BGW 50 to better track to a desired location in the vasculature of a human being. The RXT 55 shown here has a slot 53 in the top to allow it to snap on to a primary guide wire. The slot 53 may be a single width slot such as the slot 34 of the RXT 35 of FIG. 5 or it may be include tapered sections such as the tapered slot section 43 of FIGS. 7 and 9.

Figure 11:
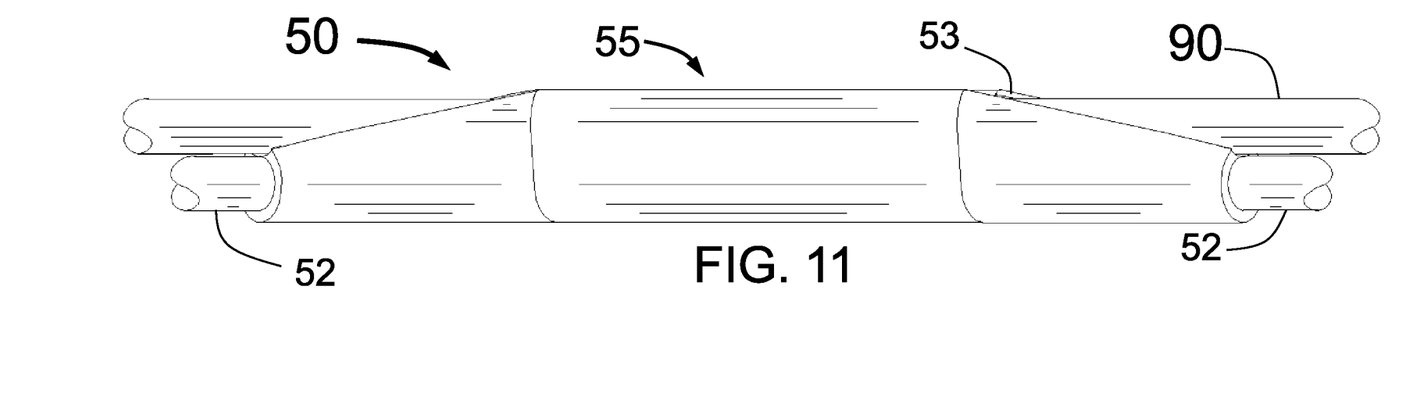
FIG. 11 is a schematic view of the embodiment of the BGW of FIG. 10 shown snapped on to a primary guide wire.

FIG. 11 is a schematic view of the BGW 50 of FIG. 10 shown placed over a primary guide wire 90.

Figure 12:
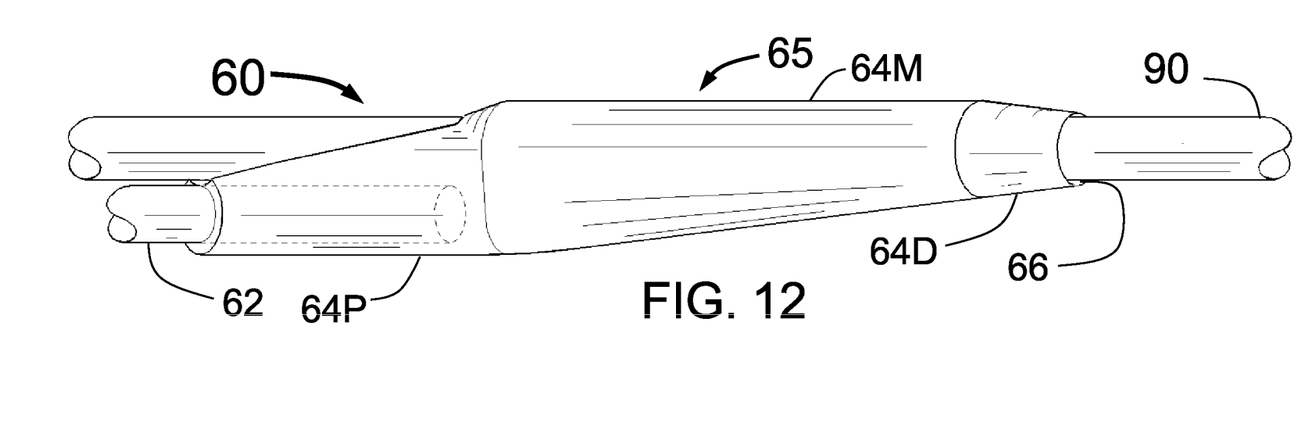
FIG. 12 is a schematic view of the preferred embodiment of the BGW with a tapered distal end FIG. 13. is a schematic view of an additional embodiment of the BGW having an pre-deployment inflatable balloon proximal to the RXT.

FIG. 12 is a schematic view of the preferred embodiment of the BGW 60 shown placed over a primary guide wire 90. The BGW 60 has a main guide wire 62, and a tapered RXT 65 having tapered proximal section 64P, central section 64M and tapered distal section 64D to facilitate tracking over the primary wire 90 as the BGW 60 is advanced to a desired location in the vasculature of a human being. The central section 64M of the RXT 65 shown here has a is tubular lumen 66 similar to the lumen 26 of the RXT 25 of FIG. 3.

The main wire 62 is attached to the RXT 65 within the proximal section 64P. The RXT 65 is to be formed from a plastic. One embodiment could have a softer or lower durometer plastic used to facilitate tracking over the primary guide wire 90

Figure 13:
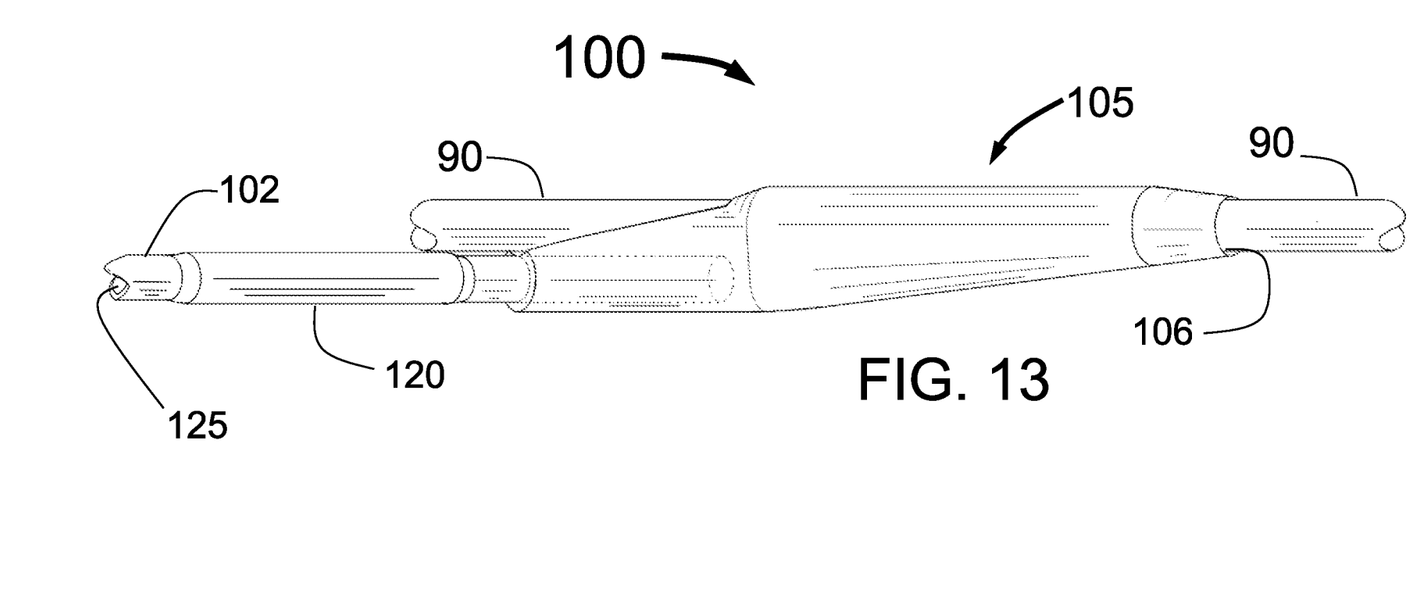

FIG. 13. is a schematic view of an embodiment of the BGW 100 with RXT 105 having an pre-deployment inflatable balloon 120 located on the tubular main guide wire 102 with balloon inflation lumen 125. The RXT 105 is identical to that of the RXT 65 of FIG. 12 having a guide wire lumen 106 through which is passed the primary guide wire 90.

Figure 14:
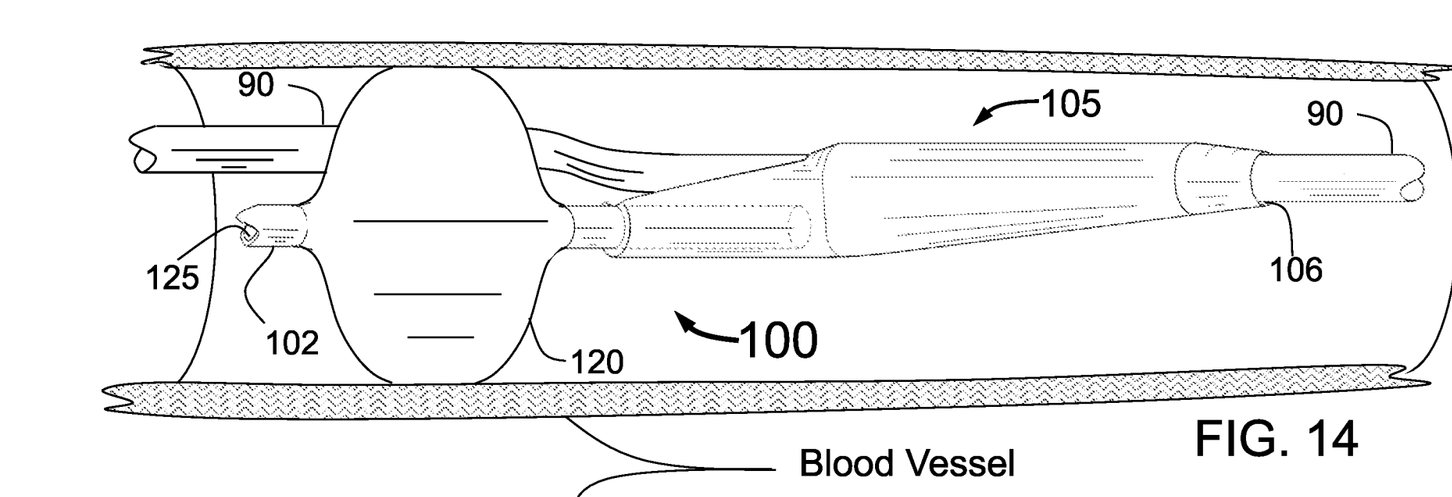
FIG. 14 is a schematic view of the embodiment of the BGW of FIG. 13 with the balloon inflated to trap the primary guide wire against the wall of a blood vessel.

FIG. 14 is a schematic view of the embodiment of the BGW 100 of FIG. 13 with the balloon 120 inflated to trap the primary guide wire 90 which passes through the guide wire lumen 106 against the wall of a blood vessel. The purpose of the balloon 120 and its ability to trap the primary guide wire 90 is that it will anchor the distal portion of the primary guide wire at a location at or past a place in the blood vessel where it may be difficult to place a catheter (not shown) due to curvature or tortuosity. Anchoring the distal end of the primary guide wire 90 will prevent it from backing out of the vessel and improve the ability to advance a catheter to the desired location.

Figure 15:
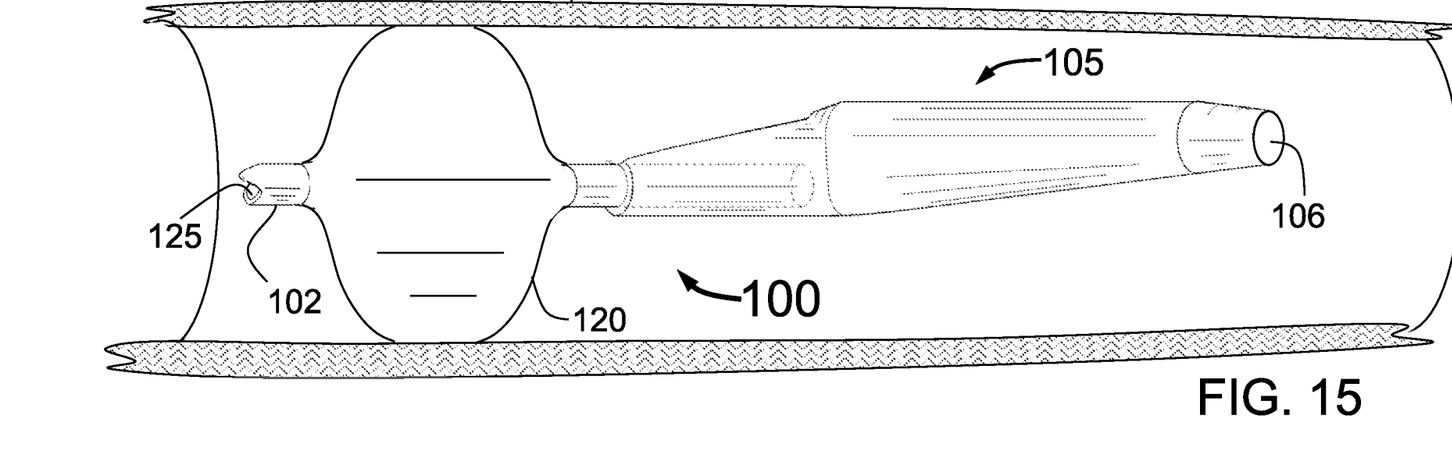
FIG. 15 is a schematic view of the embodiment of the BGW of FIG. 13 with the balloon inflated to anchor the main guide wire of the BGW at a site in the vasculature and facilitate delivery of a catheter over the main guide wire.

FIG. 15 shows the BGW 100 with the primary guide wire 90 removed and the balloon 120 inflated using the inflation lumen 125 in the main guide wire tube 102. This configuration may be the preferred one to provide an anchored guide wire for placement of a catheter in a highly curved or tortuous vessel. The method for using the BGW 100 in this configuration is as follows:

1. advance the BGW 100 over the primary guide wire 90 of FIG. 13 to a location distal to the site to be treated,
2. remove the primary guide wire 90,
3. inflate the balloon 120 against the wall of the blood vessel to anchor the distal portion of the BGW 100,
4. advance the treatment catheter over the main guide wire 102 of the BGW 100 until it is positioned at the desired treatment site proximal to the balloon 120,
5. deflate the balloon 120 to allow blood to flow again,
6. use the treatment catheter for its intended purpose,
7. if additional treatment catheters are used, the balloon 120 may be reinflated to anchor the distal portion of the BGW 100 if needed.
8. remove the treatment catheter,
9. remove the BGW 100.

The balloon 120 may be a wrapped angioplasty type balloon. If also used for balloon angioplasty the balloon should be non-compliant or semi-compliant. If only used for anchoring, the balloon should be semi-compliant or compliant. It is envisioned that using a semi-compliant balloon could allow the BGW 100 to have several important uses including:
1. Use as a buddy wire to advance a stiffer or less stiff wire easily to a site in the vasculature,
2. Using the anchoring feature of the BGW 100 to facilitate delivery of a catheter to a location otherwise difficult to access (anchoring wire) and
3. Using the balloon 120 as an angioplasty balloon to pre or post dilate an obstruction in a blood vessel.

Figure 16:
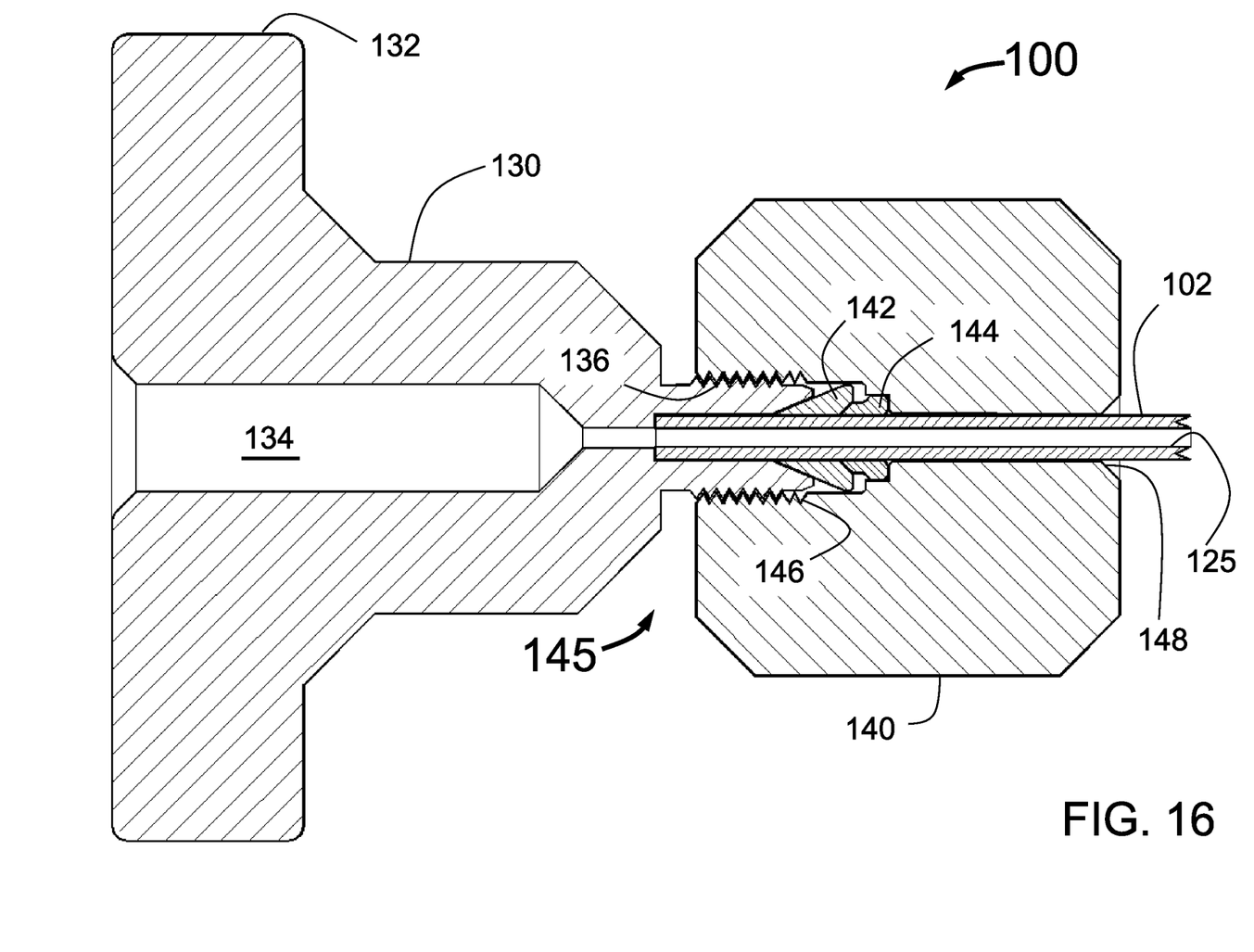
FIG. 16 is a longitudinal cross section of the proximal end of the BGW of FIG. 13 including a Swagelok® type fitting allowing balloon inflation with a removable Luer connection.

For use in trapping a primary guide wire as shown in FIG. 14 or balloon dilation a standard Luer connection at the proximal end of the BGW 100 is envisioned but if the BGW 100 is to be used as in FIG. 15 to secure the distal end of the BGW 100 in the vessel as well as advance a catheter (not shown) over the main guide wire tube 102 then a removable proximal balloon inflation fitting is needed as shown in FIG. 16.

FIG. 16 is a longitudinal cross section of the proximal end of the BGW 100 of FIG. 13 including a Swagelok® type fitting 145 allowing balloon inflation with a proximal Luer fitting 132 that is attachable to the proximal end of the main guide wire tube 102 with lumen 125 after the BGW 100 has been placed over the primary guide wire 90 of FIG. 14. The proximal fitting 145 has a proximal section 130 with a lumen 134, proximal Luer fitting 132 and distal threaded section 136. The distal nut 140 of the fitting 145 has a lumen 148 and threads 146 designed to be screwed onto the threads 136 of the proximal section 130. As with typical Swagelok fittings that are used for connections to metal tubes that can handle pressured liquids, there are two ferrules used to seal against the tube 102. These are the front ferrule 142 and back ferrule 144.

This proximal fitting 145 would be used with a catheter as follows:
1. Place a primary guide wire 90 (of FIG. 14) at the desired site in a vessel of a human body using standard techniques. For coronary placement a femoral or radial approach are typical.
2. Insert the proximal end of the primary guide wire 90 into the lumen 106 of the BGW 100 RXT 105 of FIGS. 13, 14 and 15.
3. Advance the BGW 100 over the main guide wire 90 until it is at a desired site near the distal end of the main guide wire 90.
4. Insert the proximal end of the main guide wire tube 102 into the distal guide wire lumen of the catheter to be advanced.
5. Advance the catheter until the proximal end of the main guide wire tube 102 exits from the proximal end of the catheter guide wire lumen.
6. Attach the proximal fitting 145 to the proximal end of the main guide wire tube 102 by inserting the tube 102 into the fitting 145 and tightening the nut 140 which will swage the two ferrules 142 and 144 to form a pressure seal against the tube 102.
7. Attach a balloon inflation device to the Luer fitting 132 of the proximal fitting 145.
8. Inflate the distal balloon 120 of FIG. 15 to secure the distal end of the BGW 100 at a position distal to the treatment site in the target vessel.
9. Advance the catheter over the main guide wire tube 102 to the desires site which is facilitated by the secured distal portion of the BGW 100.
10. Use the catheter to perform the desired procedure.
11. Retract the catheter and then deflate the balloon 120 and remove the BGW from the body.

Alternately, if multiple catheters are needed and the vessel is a coronary artery, multiple catheters may be needed. To exchange catheters, the balloon 120 would be deflated, the proximal fitting 145 would be removed then reattached and the balloon could be re-inflated if needed. It is also envisioned that the balloon 120 could be deflated to allow blood flow once the treatment catheter is at the desired site.

Figure 17:
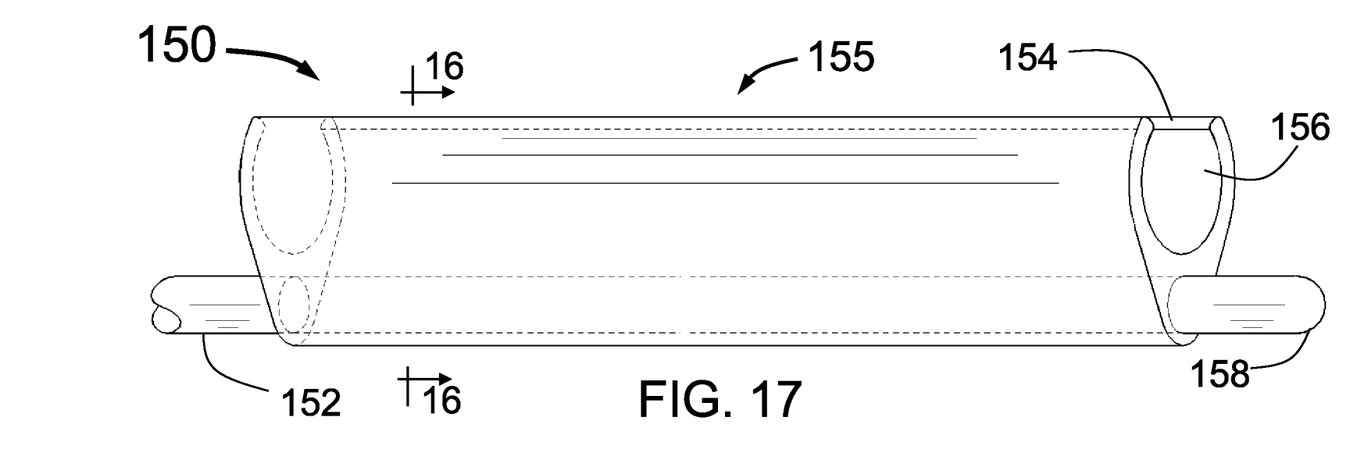
FIG. 17 is a schematic view of an embodiment of the BGW designed to be placed over a larger diameter guide wire or a catheter allowing the BGW to be advanced to a desired site within a vessel of the human body.

FIG. 17 is a schematic view of the BGW 150 with Rapid Exchange Tube 155 fixedly attached to the main wire 152 with distal end 158. The BGW 150 is designed to be placed over a larger diameter guide wire or a catheter allowing the BGW 150 to be advanced to a desired site within a vessel of the human body.

For example, in the periphery an n 0.035" guide wire is often used but to exchange it for a 0.014" guide wire needed for some devices such as drug eluting stents, the BGW 150 could be useful. Another use for the BGW 150 is with the Svelte Slender® stent-on-a-wire that has a fixed guide wire instead of being advanced over a wire like typical stent delivery systems. If a problem were to occur like a dissection and there would be need to get guide wire through the dissection, the BGW 150 would be ideal. In fact the 0.032 profile of the Svelte Slender® would allow the same dimensional BGW 100 as would be used for advancing over an 0.035" guide wire.

The embodiment of the BGW 150 shown in FIGS. 15 and 16 includes a slot 154 above the lumen 156 to allow the RXT 155 to be snapped onto another guide wire or catheter similar to the RXTs 35, 45 and 55 of FIGS. 5 through 11. It is envisioned that the slot 154 can be as shown or could be a tapered slot such as that shown for the RXT 45 of FIGS. 7, 8 and 9. It is also envisioned that a tubular version similar to the RXTs 25 and 65 of FIGS. 1 and 12 could be used for guide wire exchange and for emergency bail out where one would cut the proximal end off the catheter leaving only the shaft over which the RXT can be placed.

Figure 18:
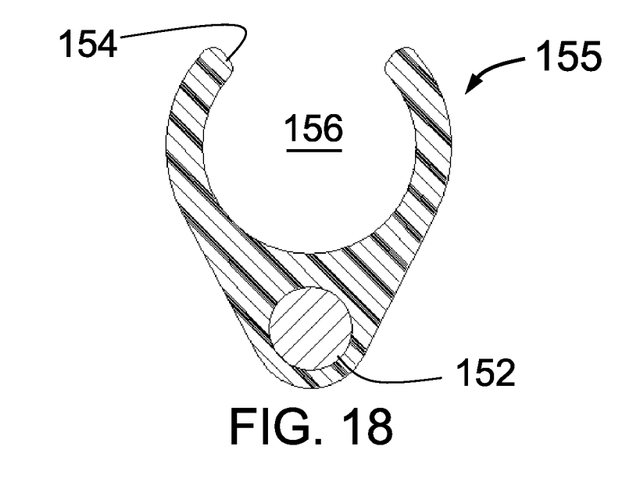
FIG. 18 is a cross section view of the RXT of the BGW of FIG. 16.

FIG. 18 is a cross section view of the RXT 155 of the BGW 150 of FIG. 17 showing it attached to the main guide wire 152 and having the lumen 156 with slot 154. The main guide wires 12, 22, 32, 42, 52, 62, 102 and 152 of FIGS. 1-17 would be 10 or 14 mil diameter for coronary use and 14, 18 or 35 mil for peripheral vascular use. They may be solid steel, or wire wrapped for flexibility. They may be lubricity coated.

The length L of the lumens 16, 26, 36, 46, 56, 66 and 106 of FIGS. 1-15 would typically be between 1 and 10 cm long and would have a diameter sized to allow passage of a primary guide wire. Different versions of the RXT are envisioned for coronary guide wires of 10 and 14 mil diameter and peripheral guide wires of 18 and 35 mil diameters.

Figure 19:
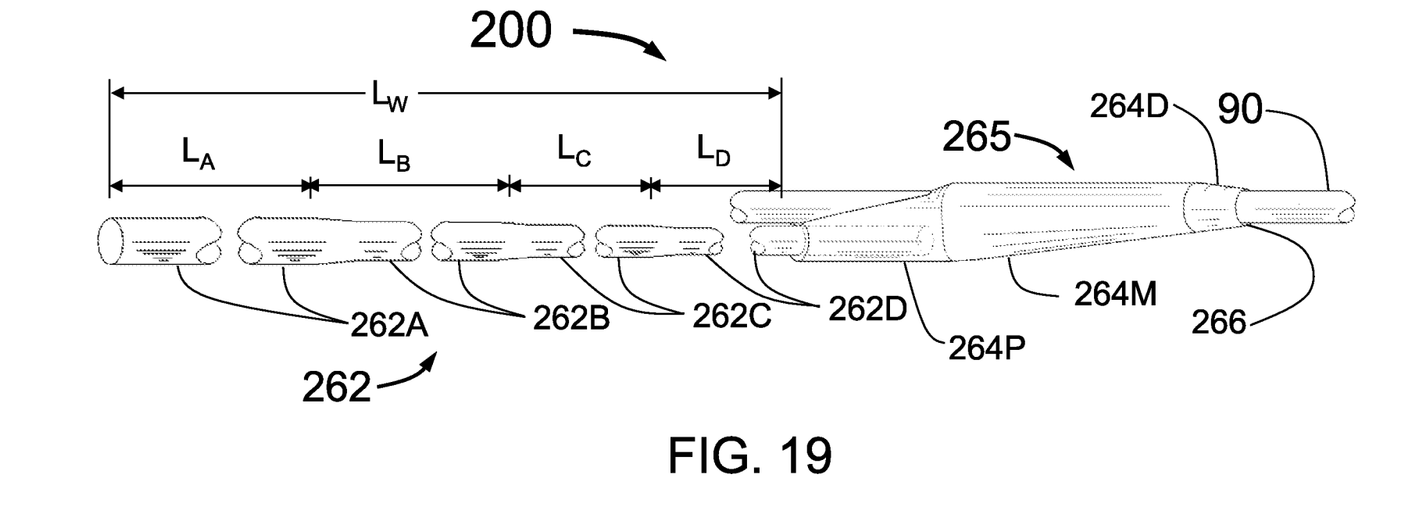
FIG. 19 is a schematic view of a multi-diameter buddy wire designed to facilitate guiding catheter exchanges.

FIG. 19 is a schematic view of a multi-diameter buddy wire (MDBW) 200 designed to facilitate guiding catheter exchanges. The MDBW 200 is designed to be advanced and retracted over a primary guide wire 90.

The MDBW 200 has a main guide wire 262, and a tapered Rapid Exchange Tip (RXT) 265 having tapered proximal section 264P, central section 264M and tapered distal section 264D to facilitate tracking over the primary wire 90 as the BGW 200 is advanced to a desired location in the vasculature of a human being. The central section 264M of the RXT 265 shown here has a is tubular lumen 266 similar to the lumen 26 of the RXT 25 of FIG. 3.

The main wire 262 is attached to the RXT 265 within the proximal section 264P. The RXT2 265 is to be formed from a plastic. One embodiment could have a softer or lower durometer plastic used to facilitate tracking over the primary guide wire 90.

The ability of the MDBW 200 to be used to exchange one guiding catheter for another as described below is facilitated by the main wire 262 having multiple wire sections 262A through 262D, each of different diameters and/or stiffness. Ideally for guiding catheter exchange, the total length $L_W$ of the main wire 262 should be similar to exchange length wires or at least 2 meters. An embodiment with 4 main wire sections is shown in FIG. 19 although a viable design could be accomplished with 2 or more sections.

In FIG. 19 for example, the diameter of section 262A would be 0.035", section 262B would be 0.025", section 262C would be 0.018" and section 262D would be 0.014". For example, the lengths $L_A$, $L_B$, $L_C$, and $L_D$, would be 200 cm, 50 cm, 30 cm and 20 cm, respectively.

If only 3 sections, 262A, 262B and 262C are used, an example of the diameters would be for section 262A would be 0.035", section 262B would be 0.018" and section 262C would be 0.014". $L_A$, $L_B$, and $L_C$, could be 240, 40 cm and 20 cm, respectively.

It is also envisioned that instead of increasing the diameter, sections of different stiffness could be used, with the stiffer sections proximal. A combination of both different diameters and stiffness is also envisioned.

An example of the method of use of the MDBW 200 in FIG. 19 is:
1) Advance the MDBW 200 over an already placed primary coronary guidewire 90 such that the distal portion RXT 265 of the MDBW 200 is close to the distal end of the already placed coronary guidewire 90.
2) Remove the previously placed primary coronary guidewire 90, leaving the MDBW 200 in place, with the main guide wire 262 distal section 262D in the coronary artery and the stiffer sections 262A, 262B and 262C in the guiding catheter (not shown).
3) Slowly, and under fluoroscopic guidance perform a half exchange by slowly removing the existing guiding catheter from the coronary and eventually over the long (exchange length) MDBW 200, remove the guiding catheter from the body completely.
4) Over the main wire 262 of the MDBW 200, slowly advance, under fluoroscopic guidance, a new and preferred guiding catheter, completing the half exchange and advancing the new guiding catheter to engage the ostium of the target coronary artery.
5) At this point one can place a new primary wire into the target vessel with the operator's choice of coronary guidewire.
6) Complete the coronary intervention using the new and preferred guiding catheter.

Figure 20:
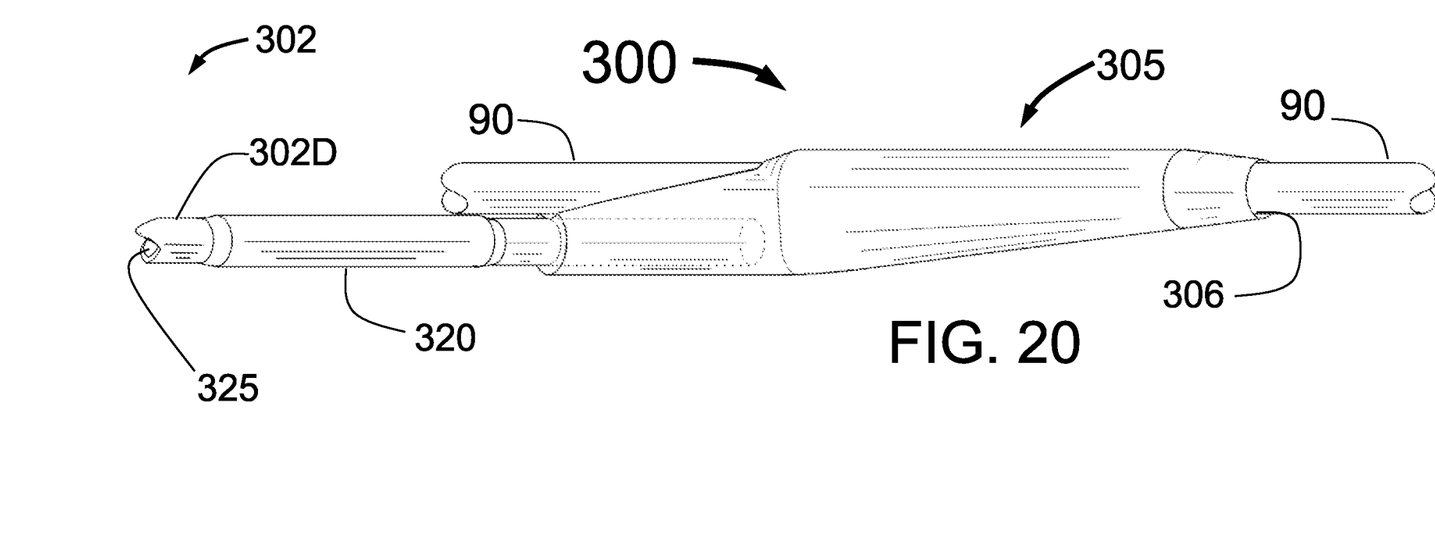
FIG. 20 is a schematic view of a multi-diameter buddy wire having a distal inflatable balloon designed to facilitate guiding catheter exchanges.

FIG. 20. is a schematic view of the distal portion of an embodiment of the MDBW 300 with RXT 305 having a pre-deployment inflatable balloon 320 located on the tubular main guide wire 302 with balloon inflation lumen 325. The purpose of the balloon 320 is to allow the distal portion of the MDBW 300 to be anchored in a vessel of a human body so that it is easier to exchange a guiding catheter over the MDBW 300 as compared to an unanchored version such as the MDBW 200 of FIG. 19.

The RXT 305 is identical to that of the RXT 265 of FIG. 19 having a guide wire lumen 306 through which is passed the primary guide wire 90.

Shown is the distal section 302D of the main guide wire 302. Not shown are the proximal sections of the multi-diameter main wire which are similar to sections 262A, 262B and 262C of the main guide wire 262 of FIG. 200 with the addition of a balloon inflation wire lumen 325 that runs all the way to the proximal end of the main guide wire 302. A removable inflation device as shown in FIG. 16 would be used to inflate and deflate the balloon 320 through the balloon inflation lumen 325. The lengths and diameters of the sections of the main wire 302 are envisioned to have the same ranges as the MDBW 200 of FIG. 19.

An example of the method of use of the MDBW 200 in FIG. 19 is:
1) Advance the MDBW 300 over an already paced primary coronary guidewire 90 such that the distal portion of the RXT 305 is close to the distal end of the already placed primary guidewire 90.
2) Remove the previously placed primary coronary guidewire 90, leaving the MDBW 300 in place, with the main guide wire 302 distal portion 302D in the coronary artery and the stiffer proximial section(s) in the guiding catheter (not shown).
3) Inflate the anchoring balloon 320 through the inflation lumen 325 in the main guide wire 302 of the MDBW 300.
4) Slowly, and under fluoroscopic guidance perform a half exchange by slowly removing the existing guiding catheter from the coronary and eventually over the long (exchange length) MDBW 300, remove the guiding catheter from the body completely.
5) Over the MDBW 300 slowly advance, under fluoroscopic guidance, the new and preferred guiding catheter, completing the half exchange and advancing the new guiding catheter to engage the ostium of the target coronary artery.
6) Deflate the anchoring balloon 320 of the MDBW 300.
7) At this point one can rewire the target vessel with the operator's choice of coronary primary guidewire 90.
8) Complete the coronary intervention using the new and preferred guiding catheter It is also envisioned that with either the MDBW 200 or MDBW 300 one would not need to remove the previously place primary coronary guidewire 90 but could leave it in place during the catheter exchange. This would add efficiency and eliminate step 2 in both methods above as well as eliminating the need to rewire the target vessel (step 5 for the MDBW 200 and Step 7 for the MDBW 200).

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A buddy guide wire comprising:
a main guide wire, and
a rapid exchange tube fixedly attached to the main guide wire at a location near a distal end of the main guide wire, the rapid exchange tube having a proximally-tapered proximal section and a distally-tapered distal section, the rapid exchange tube including a 360 degree tubular lumen with a longitudinal axis, the 360 degree tubular lumen configured to allow the rapid exchange tube to be longitudinally advanced and retracted over a guidewire having a cylindrical portion with the cylindrical portion having a diameter of less than 0.05 inches, wherein the proximally-tapered proximal section has a slot located proximal to a proximal end of the 360 degree tubular lumen, wherein the 360 degree tubular lumen has a cut configured to be opened for placement over a guide wire or catheter inserted into the slot.

2. The buddy guide wire of claim 1 where the rapid exchange tube lumen has a diameter of less than 0.04 inches.

3. The buddy guide wire of claim 1 where the rapid exchange tube lumen has a diameter of less than 0.02 inches.

4. The buddy guide wire of claim 1 where the guidewire has a diameter of less than 0.15 inches.

5. The buddy guide wire of claim 1 where the guidewire has a diameter of less than 0.10 inches.

6. The buddy guide wire of claim 1, further comprising a distal slot.

7. The buddy guide wire of claim 1 where the tapered distal section of the rapid exchange tube has taper that is smaller at a distal end of the rapid exchange tube.

8. The buddy guide wire of claim 1 where the main guide wire has a central lumen.

9. The buddy guide wire of claim 8 further including an inflatable balloon proximal to rapid exchange tube with the central lumen of the main guide wire being a balloon inflation lumen.

10. The buddy guide wire of claim 9 further including a balloon inflation port attached to the proximal end of the main guide wire.

11. The buddy guide wire of claim 10 where the proximal balloon inflation port is separate and is attachable over the proximal end of the main guide wire.

12. The buddy guide wire of claim 10 where the proximal balloon inflation port includes two ferrules in a fitting configured to provide a pressure seal against a proximal portion of the main guide wire.

13. The buddy guide wire of claim 1 where the main guide wire has at least two sections, a distal section and a proximal section, with the distal section being of smaller diameter than the proximal section.

14. The buddy guide wire of claim 13 where the main guide wire has at least three sections, a distal section, a central section and a proximal section where the distal section is of smaller diameter than the central section and the central section is of smaller diameter than the proximal section.

15. The buddy guide wire of claim 13 where the distal section diameter is at most 0.018".

16. The buddy guide wire of claim 1 where the main guide wire has at least two sections, a distal section and a proximal section, with the distal section being more flexible than the proximal section.

17. The buddy guide wire of claim 16 where the main guide wire has at least three sections, a distal section, a central section and a proximal section where the distal section is more flexible than the central section and the central section is of more flexible than the proximal section.

18. A buddy guide wire comprising:

a main guide wire; and a rapid exchange tube fixedly attached to the main guide wire at a location near a distal end of the main guide wire, the rapid exchange tube having a proximally-tapered proximal section, a distally-tapered central section having a 360 degree tubular lumen with a longitudinal axis, and a distally-tapered distal section, wherein the distally-tapered distal section is more tapered the distally-tapered central section, the 360 degree tubular lumen configured to allow the rapid exchange tube to be longitudinally advanced and retracted over a guidewire having a cylindrical portion with the cylindrical portion having a diameter of less than 0.05 inches, wherein the proximally-tapered proximal section has a proximal slot located proximal to a proximal end of the 360 degree tubular lumen and the distally-tapered distal section has a distal slot, wherein the 360 degree tubular lumen has a cut configured to be opened for placement over a guide wire or catheter inserted into the proximal or distal slot.

19. A buddy guide wire comprising:

a main guide wire; and a rapid exchange tube fixedly attached to the main guide wire at a location near a distal end of the main guide wire, the rapid exchange tube having a proximally-tapered proximal section and a distally-tapered distal section, the rapid exchange tube including a 360 degree tubular lumen with a longitudinal axis, the 360 degree tubular lumen configured to allow the rapid exchange tube to be longitudinally advanced and retracted over a guidewire having a cylindrical portion with the cylindrical portion having a diameter of less than 0.05 inches, where the rapid exchange tube further includes a slot on the proximally-tapered proximal section that is configured to allow the guidewire to be pushed into the lumen of the rapid exchange tube through the slot, and wherein the distally-tapered distal section has a distal slot, wherein the 360 degree tubular lumen has a cut configured to be opened for placement over a guide wire or catheter inserted into the slot.

* * * * *